United States Patent [19]
Haridas

[11] Patent Number: 5,808,140
[45] Date of Patent: Sep. 15, 1998

US005808140A

[54] PROCESS FOR MAKING MESNA, DIMESNA AND DERIVATIVES THEREOF

[75] Inventor: Kochat Haridas, San Antonio, Tex.

[73] Assignee: BioNumerik Pharmaceuticals, Inc., San Antonio, Tex.

[21] Appl. No.: 935,463

[22] Filed: Sep. 24, 1997

Related U.S. Application Data

[60] Provisional application No. 60/028,212 Oct. 1, 1996.
[51] Int. Cl.$^6$ ........................................................ C07F 9/38
[52] U.S. Cl. .................................... 562/8; 562/20; 562/30; 562/101; 562/103; 562/108; 568/26; 568/18
[58] Field of Search ................................. 562/20, 8, 101, 562/103, 108, 30; 568/26, 18

[56] References Cited

U.S. PATENT DOCUMENTS 3,994,979 11/1976 Warner .

OTHER PUBLICATIONS

CA:122:264627, abs of "The synthesis of unsymmetric and symmetric disulfides", Ternay, Phosphorus ,Sulfur Silicon Rel Elem, 95&96 (1–4), pp. 1042–6507, 1994.

CA:67:90729, abs of "Synthesis of water–soluble trisulfides", Fedoseeva, Ukr. Khim. Zh., 33(6), pp. 596–597, 1967.

CA:103:37096, abs of SU1130561 Dec. 1984.

*Primary Examiner*—Gary Geist
*Assistant Examiner*—Jean F. Vollano
*Attorney, Agent, or Firm*—Thomas J. Dodd

[57] ABSTRACT

A process for synthesizing disulfides and sulfhydryl compounds which are useful pharmaceuticals. The process includes a two step, single pot process for preparing disulfides from an alkenyl sulfonate salt. The disulfides are useful as toxicity mitigating agents of chemotherapeutic drugs, such as certain platinum complexes, and as use therapeutic drugs for a variety of conditions in mammals.

The two step process involves first the conversion of the starting reagent to a mercaptane sulfonate, then an oxidation to the desired disulfide.

4 Claims, No Drawings

PROCESS FOR MAKING MESNA, DIMESNA AND DERIVATIVES THEREOF

FIELD OF THE INVENTION

This invention relates to a novel process for making the chemotherapeutic protective agents, sodium 2-mercaptoethane sulfonate (mesna), disodium 2,2'-dithiobis ethane sulfonate (dimesna) and derivatives thereof.

BACKGROUND OF THE INVENTION

Disodium 2,2'-dithiobis ethane sulfonate (dimesna), and other salts and derivatives thereof, are known chemotherapeutic protective agents used to mitigate the toxicity of platinum complex antitumor drugs which are given to patients with certain types of cancer. Disclosure of dimesna and like compounds as platinum protecting agents are found in U.S. application Ser. No. 08/338,379, filed Nov. 14, 1994, U.S. application Ser. No. 08/553,005, filed Nov. 3, 1995, and elsewhere in the literature.

Dimesna is a physiological auto-oxidation product of sodium 2-mercaptoethane sulfonate (mesna), which is also a protective agent for chemotherapeutic drugs. The structures of the preferred sodium salts (disodium in the case of the dianionic dimesna molecule) of mesna and dimesna are seen below as formula I and formula II, respectively.

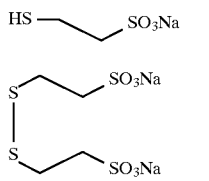

Both mesna and dimesna have been used with varying degrees of success as protective agents for administration with platinum complex anti-tumor drugs. In particular, dimesna has been shown to be effective in providing protection against cisplatin (cis-diammine dichloro platinum) induced nephrotoxicity, and both mesna and dimesna have been shown to be effective against carboplatin (cis-diammine-1,1 cyclobutane dicarboxylato platinum) induced myelosuppression. Mesna has also been used as a protective agent with other antitumor drugs, and is approved for such use in the United States and a number of foreign jurisdictions. Full disclosures on the action of mesna, dimesna, and derivatives of each is found in one or more of the above referred documents, and more may also be found in the published literature. The wide-ranging utility of both mesna and dimesna as protective agents has been established in this art.

As mentioned above, mesna is auto-oxidized in the body to dimesna under mildly basic conditions and in the presence of oxygen, such as those present in plasma. Prior synthetic methods of making dimesna involved the oxidation of mesna to form its dimer (dimesna) in substantially quantitative yield. This synthesis was accomplished by reacting the dissolved mesna with an oxidizing agent which contained a source of elemental iodine as the oxidant, or in iodate form in an aqueous medium.

The prior art processes for synthesizing mesna and dimesna (and like sulfhydryls and disulfides) include the conversion of various alkyl sulfonic acids into their respective mercaptane derivatives and the subsequent oxidation into their respective disulfides by use of iodine-containing reagents as an oxidizing reagent. These processes, while efficient, required isolation procedures to be performed to isolate and purify the end products from the reagents used. Further, environmental pollutants were generated by the prior art processes which required disposal. Finally, the prior art processes could not be carried out in a single-pot process.

SUMMARY OF THE INVENTION

The process of this invention is a two-step, single pot synthetic process for making dimesna and like compounds of the following formula:

$R_1-S-R_2$;

wherein $R_1$ is hydrogen, X-lower alkyl, or X-lower alkyl-$R_3$;

$R_2$ is -lower alkyl-$R_4$;

$R_3$ and $R_4$ are each individually $SO_3M$ or $PO_3M_2$;

X is absent or X is sulfur; and

M is an alkali metal.

The process of this invention essentially involves a two step single pot synthetic process which results in the conversion of an alkenyl sulfonate salt or acid to the desired formula I compound. The process in the case of mesna is a single step process which converts the alkenyl sulfonate salt to mesna or a mesna derivative by reacting with an alkali metal sulfide or with hydrogen sulfide.

If the desired end product is dimesna or a dimesna derivative, a two-step single pot process is involved. Step 1 is as described above. Step 2 of the process is performed in the same reaction vessel as Step 1 without the need to purify or isolate the mesna formed during that step. Step 2 includes the introduction of oxygen gas into the vessel, along with an increase in pressure and temperature above ambient values, at least 20 pounds per square inch (psi) and at least 60° C., at a slightly basic pH. Dimesna or a derivative thereof is formed in essentially quantitative yield. The desired final product can be easily crystallized from the aqueous reaction medium itself.

The process of this invention represents a significant improvement over the prior art processes for synthesizing this important series of compounds. The process has been scaled up to produce multiple gram quantities of dimesna in substantially pure form.

It is therefore an object of this invention to provide for a process of making mesna, dimesna and useful derivatives thereof.

Another object of this invention is to provide for a process of making dimesna which can be carried out in a single reaction vessel.

Another object of this invention is to provide for a process of making dimesna, mesna and derivatives thereof, which is efficient, economical, and can be scaled up to produce multiple gram quantities of the desired product in substantially pure form.

DETAILED DESCRIPTION OF THE PREFERRED EMBODIMENTS

The preferred embodiments herein described are not intended to be exhaustive or to limit the invention to the precise forms or steps disclosed. They have been chosen and described to explain the principles of the invention and its application and practical uses to enable others skilled in the art to utilize and understand the teachings.

The process of this invention is characterized by a single pot process in which a starting reagent is converted to a useful sulfide, thioether or disulfide. The preferred process is shown below as Scheme I:

Scheme 1

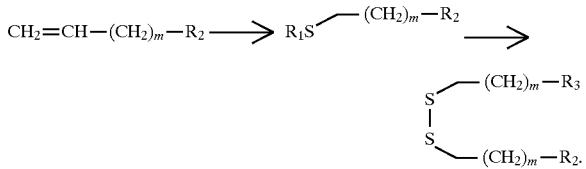

wherein $R_1$ is hydrogen, X-lower alkyl, or X-lower alkyl-$R_3$;

$R_2$ is $SO_3M$ or $PO_3M_2$;

$R_3$ is $SO_3M$ or $PO_3M_2$;

X is absent or X is sulfur;

m is 0, 1, 2 or 3; and

M is an alkali metal.

The preferred process shown is for making the dianionic salt of a dithiobis alkyl sulfonate (or phosphonate), such as dimesna. In the preferred formula I, —$(CH_2)_m$— forms a carbon chain of 1–4 total alkylidene moieties (lower alkyl), and M is an alkali metal:

$R_1$—S-lower alkyl-$SO_3M$ (I)

wherein $R_1$ is hydrogen or —S-lower alkyl-$SO_3M$; and

M is an alkali metal.

As shown in Scheme I, the starting reagent is an alkenyl sulfonate salt (or sulfonic acid) having a terminal unsaturated double bond. In the case of the synthesis of the most preferred thiol (mesna) and the most preferred disulfide (dimesna) products, the starting reagent is vinyl sodium sulfonate. Other reagents of varying carbon chain length may be substituted depending upon the desired end product. In the case of making thioethers, a free radical initiator is introduced to activate the terminal double bond.

The first step in the inventive process involves the addition of a sulfhydryl moiety in an anti-Markovnikov fashion to the unsaturated terminal double bond by generating an $sp^3$ center. The addition to the double bond is effected by reacting the starting alkenyl sulfonate salt with a hydrosulfide salt or with hydrogen sulfide, preferably in a slightly basic solution.

This step forms a sulfhydryl alkane sulfonate compound which may be recrystallized directly or carried forward to the second step of the inventive process to form the desired disulfide compound.

The second step of the process involves the oxidation of the sulfhydryl alkane sulfonate to a disulfide. This step of the process is preferably carried out in the same reaction vessel as the first step of the process and involves heating the intermediate to at least 40° C. (most preferably to at least 60° C.) and bubbling oxygen gas through the solution to enrich the reaction medium with molecular oxygen. The pressure inside the vessel is also increased above ambient pressure, preferably to at least 20 pounds per square inch, most preferably to at least 50 pounds per square inch. The end product is then recrystallized directly from the solution without need for further purification.

The end disulfide compound may be formulated with antitumor drugs, such as platinum complexes, ifosfamide, oxazaphosphorine, etoposide and others, or the compound may be packaged separately for administration with an antitumor agent. The end compound is also useful in the treatment of many other conditions, and may be packaged and distributed for administration to patients with any of the indicated conditions.

The most preferred end product is dimesna, which has proven usefulness as a protective agent for a number of recognized antitumor agents as listed above, and found throughout the literature in this field. An example of the most preferred process to synthesize dimesna is set forth below as Example 1.

If the desired end product is an alkylated derivative of mesna ($R_1$ is -lower alkyl), step 1 of the process is performed as described above. The sulfide thus produced is then taken up in a protic solvent which contains desired alkoxides. A preferred alkoxide is sodium methoxide, with the solution warmed to about 60° C. followed by the addition of the respective alkyl iodide to effect the alkylation. The thioether thus formed is generally quantitative in yield. This reaction is shown as Scheme 2, below.

Scheme 2

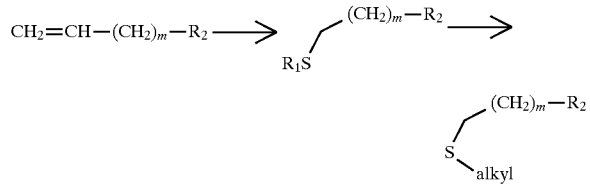

A third alternative process is used when the phosphonate derivative of mesna is preferred. In this process, shown as Scheme 3 below, the starting reagent is a halo alkyl phosphonate ester, preferably a bromo alkyl phosphonate ester.

Scheme 3

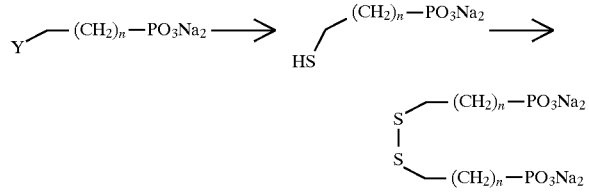

As shown in Scheme 3, the starting reagent to produce the phosphonate disulfide is a halogen tethered alkane phosphonate. In the above scheme, Y is a halogen, preferably chlorine or bromine, and n is 0 to 4, most preferably 1 or 2. The two step, single pot process involves first the treatment of the starting reagent with sodium hydrosulfide or a polysulfide at elevated temperature. Alternatively, step 1 may be achieved as stated in Scheme 2, by converting the alkenyl phosphonic acid to the sulfide by addition of the sulfur sources in the presence of a free radical initiator. Step 2, the oxidation to the disulfide, is the same as in Schemes 1 and 2, above.

The specific examples below are illustrative of the process and of the best mode of carrying out the invention, and are not intended to limit the invention.

EXAMPLE 1

Disodium 2,2'-dithiobis ethane sulfonate 100 mL of a 25% aqueous stock solution (25 grams VSA, 0.2 moles) of vinyl sulfonic acid (VSA) sodium salt (Aldrich Chemical Company) was taken up in a Parr vessel, and argon gas bubbled in for one hour to deoxygenate the aqueous solution. To this solution was added 33.5 grams (0.597 moles) of sodium hydrosulfide monohydrate (Aldrich Chemical Company) and 10 mL of sodium hydroxide. The pH of the solution was approximately 9.0. The reaction mixture was agitated over a Parr apparatus for two hours, during which time NMR monitoring was conducted at 30 minute intervals.

The product obtained from this step was taken to the next step without further purification. The product was heated to 60° C., and oxygen bubbled into the vessel for thirty minutes. The vessel was then pressurized to 50 pounds per square inch and agitated for six hours at 60° C. for six more hours.

The completed reaction was then worked up by concentrating the aqueous fraction at 80° C. using an industrial vacuum followed by diffused recrystallization from water. The crystallized product was then lyophilized after adjusting the pH to 7.2 by adding 1N HCl and filtering through a 0.2 micron pore membrane filter. NMR and elemental analysis confirmed the presence of pure (99%) sodium 2,2'-dithiobis ethane sulfonate.

EXAMPLE 2

Tetrasodium, 2, 2'-dithiobis ethane phosphonate

2-Chlorophosphonic acid (1 gram; 7 mmols) was taken up in anhydrous ethanol (10 ml) and degassed with a continuous stream of argon for at least 30 minutes. This was then added to a boiling solution of sodium hydrosulfide hydrate (1.4 g, 2.5 mmol) in ethanol to obtain a reaction mixture with a final pH of approximately 9. The resultant reaction mixture was then refluxed for 10 hours. The reaction mixture was then cooled and the pH adjusted to 8 using 1N HCl. The solvent was removed and the product was purified by diffused crystallization. The white solid was then taken into a Parr bottle and added 50 ml water. The aqueous solution was then bubbled with a stream of oxygen for a period of at least 1 hour. Then the bottle was pressurized with 50 psi oxygen and shaken at 60° C. for 4 hours. The product was isolated by concentrating the aqueous portion to half at 80° C. under industrial vacuum followed by crystallization. The product thus obtained was then characterized by high field NMR and elemental analysis and by comparing with the authentic sample obtained in earlier batches.

EXAMPLE 3

Tetrasodium 2,2'-dithiobis ethane phosphonate

2-Bromophosphonic acid (1 gram; 7 mmols) was taken up in water (10 ml) and degassed with a continuos stream of argon for at least 30 minutes. This was then added to a boiling solution of sodium hydrosulfide hydrate (1.4 g, 2.5 mmol) in water to obtain a reaction mixture with a final pH of approximately 9. The resultant reaction mixture was then refluxed for 10 hours. The reaction mixture was then cooled and the pH adjusted to 8 using 1N HCl. The aqueous portion was then concentrated and the product was purified by diffused crystallization. The white solid was then taken into a Parr bottle and added 50 ml water. The aqueous solution was then bubbled with a stream of oxygen for a period of at least 1 hour. Then the bottle was pressurized with 50 psi oxygen and shaken at 60° C. for 4 hours. The product was isolated by concentrating the aqueous portion to half at 80° C. under industrial vacuum followed by crystallization. The product thus obtained was then characterized by high field NMR and elemental analysis and by comparing with the authentic sample obtained in earlier batches.

EXAMPLE 4

Monosodium methyldithio-ethyl sulfonate

Sodium methoxide (1.5 gram) was taken up in anhydrous methanol (20 ml) and sodium mercaptoethane sulfonate (mesna) (1 g) added. The reaction mixture was then refluxed for 6 hours. To the above solution was then added methyl iodide (2 ml) and stirred for an additional 2 hours. The reaction mixture was then concentrated and the product was crystallized from water. The product was then characterized by NMR. Yield was quantitative.

$^1$H NMR (300 MHz, D$_2$O): 1.99δ (3H, s); 2.67–2.72δ (2H, m); 2.99–3.04δ (2H, m). $^{13}$C NMR: d 13.89, 27.28, 29.92, 50.31

EXAMPLE 5

Monosodium ethyldithio-ethyl sulfonate

Sodium ethoxide (1.5 gram) was taken in anhydrous ethanol (20 ml) and added monosodium mercaptoethane sulfonate (mesna) (1 g). The reaction mixture was then refluxed for 6 hours. To the above solution was then added ethyl iodide (2 ml) and stirred for an additional 2 hours. The reaction mixture was then concentrated and the product was crystallized from water. The product was then characterized by NMR. Yield of the reaction was found quantitative.

$^1$H NMR (300 MHz, D$_2$O): 1.07δ (3H, t, J=7.5 Hz); 2.45δ 92H, q, J=7.5 Hz); 2.69–2.75δ (2H, m); 2.96–3.02δ (2H, m). $^{13}$C NMR: d 12.65, 23.84, 24.05, 28.96, 49.98

The above description does not limit the invention to the details given, but may be expanded within the scope of the following claims.

What is claimed is:

1. A process for making compounds of formula I:

$$R_1\text{—}S\text{—}R_2; \qquad (I)$$

wherein

R$_1$ is hydrogen, X-lower alkyl, or X-lower alkyl-R$_3$;

R$_2$ is -lower alkyl-R$_4$;

R$_3$ and R$_4$ are each individually SO$_3$M or PO$_3$M$_2$;

X is absent, or X is sulfur;

M is an alkali metal;

said process comprising the steps of:
(i) providing a reagent of formula II and adding the formula II reagent to a vessel;

$$H_2C\text{=}CH\text{—}(CH_2)_m\text{—}R_2 \qquad (II)$$

wherein m is 0, 1, 2 or 3,;
(ii) adding to the vessel a quantity of a reagent of the formula:

$$R_5\text{—}SH,$$

wherein R$_5$ is hydrogen or an alkali metal;
(iii) pressurizing the vessel with oxygen gas to at least 20 psi, and elevating the temperature of the reagents in the vessel to at least 40° C.

2. The process of claim 1 wherein step (iii) includes pressurizing the vessel to at least 30 psi.

3. The process of claim 1 wherein R$_1$ is —S—(CH$_2$)$_2$—SO$_3$Na, and R$_5$ is Na.

4. The process of claim 1 wherein X is hydrogen.

* * * * *